United States Patent
Daugela

(10) Patent No.: US 9,753,016 B1
(45) Date of Patent: Sep. 5, 2017

(54) NANOINDENTER ULTRASONIC PROBE TIP

(71) Applicant: Nanometronix LLC, Bloomington, MN (US)

(72) Inventor: Antanas Daugela, Bloomington, MN (US)

(73) Assignee: Nanometronix LLC, Bloomington, MN (US)

( * ) Notice: Subject to any disclaimer, the term of this patent is extended or adjusted under 35 U.S.C. 154(b) by 302 days.

(21) Appl. No.: 14/510,071

(22) Filed: Oct. 8, 2014

Related U.S. Application Data

(60) Provisional application No. 61/888,317, filed on Oct. 8, 2013.

(51) Int. Cl.
*G01N 29/44* (2006.01)
*G01N 3/40* (2006.01)
*G01N 29/24* (2006.01)

(52) U.S. Cl.
CPC ............. *G01N 29/24* (2013.01); *G01N 3/405* (2013.01); *G01N 29/4409* (2013.01)

(58) Field of Classification Search
CPC .... G01N 3/08; G01N 3/42; G01N 2203/0647; G01Q 60/366; B82Y 35/00
USPC ......................................................... 73/573
See application file for complete search history.

(56) References Cited

U.S. PATENT DOCUMENTS

| | | | | |
|---|---|---|---|---|
| 5,112,248 A * | 5/1992 | Kibblewhite | ........ | H01R 4/4863 439/13 |
| 5,193,383 A * | 3/1993 | Burnham | ............... | B82Y 35/00 73/105 |
| 5,220,839 A * | 6/1993 | Kibblewhite | ......... | B06B 1/0662 73/761 |
| 6,978,664 B1 * | 12/2005 | Uchic | ...................... | G01N 3/42 73/85 |
| 7,083,589 B2 * | 8/2006 | Banko | ................. | A61F 9/00745 433/119 |
| 7,456,400 B2 * | 11/2008 | Shigeno | ................. | B82Y 35/00 250/306 |
| 7,878,071 B2 * | 2/2011 | Greer | ....................... | G01N 3/08 73/777 |
| 8,782,902 B2 * | 7/2014 | Pyun | ...................... | B24B 35/00 29/898.13 |
| 2006/0235305 A1 * | 10/2006 | Cotter | ................ | A61B 17/1604 600/459 |
| 2012/0268744 A1 * | 10/2012 | Wolf | .................. | G01B 11/0625 356/447 |

(Continued)

*Primary Examiner* — J M Saint Surin
(74) *Attorney, Agent, or Firm* — Haugen Law Firm PLLP

(57) ABSTRACT

A multimode ultrasonic probe tip and transducer integrated into a micro tool, such as a nano indenter or a nano indenter interfaced with a Scanning Probe Microscope (SPM) is described. The tip component may be utilized to determine mechanical properties or characteristics of a sample, including for example, complex elastic modulus, hardness, friction coefficient, and strain and stress at nanometer scales and high frequencies. The tip component is configured to operate at multi-resonant frequencies providing sub-nanometer vertical resolution. The tip component may be quasi-statistically calibrated and contact mechanics constitutive equations may be utilized to derive mechanical properties of a sample. Contact mechanical impedance and acoustic impedance may also be compared.

24 Claims, 15 Drawing Sheets

(56) References Cited

U.S. PATENT DOCUMENTS

2013/0098145 A1* 4/2013 Oh ..................... G01N 3/42
  73/81
2014/0090480 A1* 4/2014 Adams ................ G01N 3/42
  73/818

* cited by examiner

NANOINDENTER ULTRASONIC PROBE TIP

CROSS-REFERENCE TO RELATED APPLICATIONS

This application claims the filing benefit and priority of U.S. Provisional Application Ser. No. 61/888,317 filed Oct. 8, 2013, the contents which are incorporated herein by reference in its entirety.

FEDERAL SPONSORSHIP

Not Applicable

JOINT RESEARCH AGREEMENT

Not Applicable

TECHNICAL FIELD

This invention pertains generally to probe tips and more particularly to a probe tip that may be utilized in nano scale micro tools including Nano-indenters, Scanning Probe Microscopy (SPM), Atomic Force Microscopy (AFM), Scanning Electron Microscopy (SEM), Transmission Electron Microscopy (TEM), combinations thereof, or other similar tools. The probe tip of the invention utilizes propagation of longitudinal resonant frequency waves through the tip to determine and compare acoustic contact impedance with electromechanical impedance of a sample.

BACKGROUND

Prior micro tools are capable of determining certain characteristics of a material, however the prior known tools include limitations that are overcome by the present invention. For example, quantitative nano scale characterization devices such as Atomic Force Microscopes (AFM) and other mechanical cantilever based systems are very effective at imaging a surface of a sample at nanometer and sub-nanometer scales, however because of the required variable tip geometry these tools are not suitable to simultaneously determine, with the same probe tip, mechanical properties of the sample. Further, although AFM devices are also operable in a tapping mode or other modes that utilize resonance modes of the AFM cantilever, these modes are also not capable of rendering material properties of a sample, such as elasticity modulus or sample hardness.

Other micro tools such as a quantitative nano indenter may derive elastic contact properties of a sample, however these tools are limited to quasi-static response. Further, the typical electrostatic or voice coils used for actuation and sensing in nano indenters limit the tool's dynamic response based complex modulus characterization technique to bandwidths of 250 Hz or less. Others have described a nano indenter that utilizes a millimeter scale impedance shaker head having a flat frequency response for operational bandwidth up to 1000 Hz. Also, a prior impedance head based system was applied at sub-millimeter size contacts where the complex modulus characterization was derived in-situ from random impulses by means of an FFT analyzer. However, these devices do not describe an interchangeable probe tip that may be utilized to determine nano indentation hardness, elasticity modulus, surface hardness imaging, group velocities, elasticity constants, phase transformation, onset of plasticity, twining, thin film fractures, electrical resistance, surface topology, and other material characteristics of a sample.

SUMMARY

Embodiments according to aspects of the invention include a combination micro tool probe tip and ultrasonic transducer capable of transmitting longitudinal resonant high frequency ultrasonic waves to determine time-dependent properties of a multilayered sample such as complex modulus, adhesion, or a coefficient of friction. These material characteristics may be evaluated for thin films, bulk materials, and eutectic alloys alike with the use of the present invention's multi-mode ultrasonic transducer interfaced with a nano indentation device and Scanning Probe Microscopy. A preferred resolution may be obtained by changing different longitudinal vibrations and torsional oscillation modes of the multi-mode ultrasonic transducer in contact with the sample. The obtained output signal represents acoustic impedance of the sample which is a function of the material properties such as storage and loss modulus, hardness, adhesion, friction coefficient and stress and strain.

Also described herein is an ultrasonic tip system for metrology and topology type tools. The ultrasonic tip system includes a probe tip, a comparator, a wave guide, and an energy source. The probe tip includes an ultrasonic transducer that directs ultrasonic waves towards a sample and an elongated wave guide coupled to the ultrasonic transducer, wherein the wave guide vibrates longitudinally and oscillates rotationally dependent upon a frequency of the ultrasonic waves from the ultrasonic transducer. The comparator compares obtained contact acoustic impedance with measured electromechanical impedance which may be utilized to determine mechanical characteristics of a sample. In the system of the invention the transducer propagates ultrasonic waves at a resonant frequency with a range of frequencies between 100 kHz to 2 MHz. Those skilled in the art will appreciate that certain resonant frequencies wave propagations may be preferred dependent upon the material characteristic being determined.

Further described herein is an ultrasonic tip component for a micro tool. The tip component includes an elongated column having a free distal end, a base from which the elongated column extends, an ultrasonic transducer coupled to the base on a side opposing the elongated column, and a coupling member for coupling the base of the tip to the tool. A control system may be coupled to the ultrasonic transducer to control resonant frequency waves generated by the ultrasonic transducer and to control a determination of mechanical characteristics of a sample.

Embodiments according to aspects of the invention also include a method of determining material characteristics of a sample. The method may include the steps of coupling a tip component to a micro tool (wherein the tip component includes an elongated column having a free distal end, a base from which the elongated column extends, an ultrasonic transducer coupled to the base on a side opposing the elongated column, and a coupling member for coupling the base of the tip to the tool), contacting the free distal end of the tip component with a sample, activating the ultrasonic transducer, calibrating the ultrasonic transducer, processing waves received by the transducer, and determining a characteristic of the sample. The calibrating step may further include adjusting the ultrasonic transducer so that waves propagate through the elongated column at a resonant frequency with a range of frequencies between 100 kHz to 2

MHz. The calibrating step may further include determining boundary conditions for the resonant frequency. The method of the invention may also include surface scanning the sample while determining sample characteristics. The method of the invention may also include generating an approximation of a topology of the sample dependent upon signals received by the ultrasonic transducer.

The accompanying drawings, which are incorporated in and constitute a portion of this specification, illustrate embodiments of the invention and, together with the detailed description, serve to further explain the invention. The embodiments illustrated herein are presently preferred; however, it should be understood, that the invention is not limited to the precise arrangements and instrumentalities shown. For a fuller understanding of the nature and advantages of the invention, reference should be made to the detailed description in conjunction with the accompanying drawings.

DESCRIPTION OF THE DRAWINGS

In the various figures, which are not necessarily drawn to scale, like numerals throughout the figures identify substantially similar components.

DETAILED DESCRIPTION

The following description provides detail of various embodiments of the invention, one or more examples of which are set forth below. Each of these embodiments are provided by way of explanation of the invention, and not intended to be a limitation of the invention. Further, those skilled in the art will appreciate that various modifications and variations may be made in the present invention without departing from the scope or spirit of the invention. By way of example, those skilled in the art will recognize that features illustrated or described as part of one embodiment, may be used in another embodiment to yield a still further embodiment. Thus, it is intended that the present invention also cover such modifications and variations that come within the scope of the appended claims and their equivalents.

Figure 1:
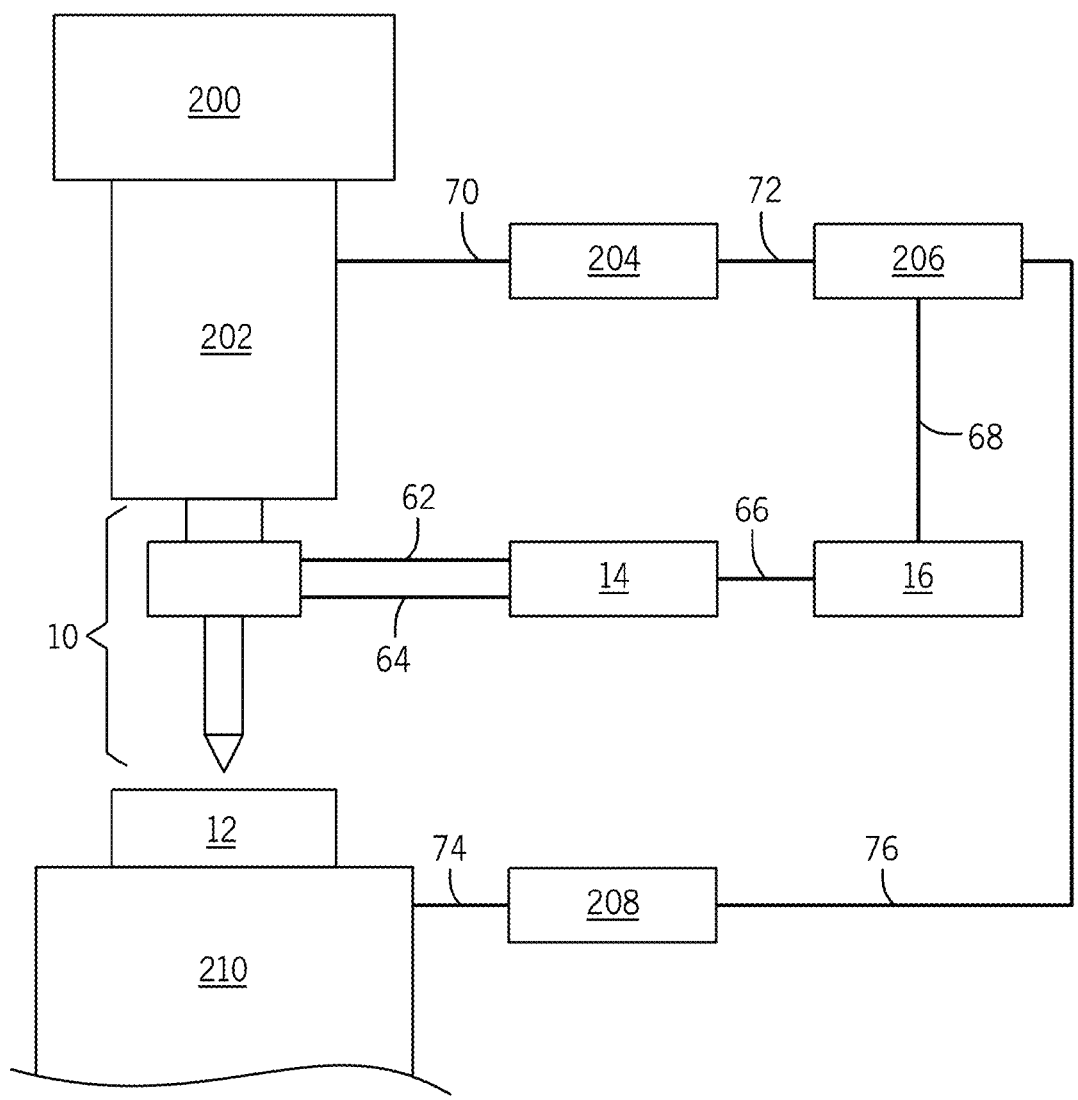
FIG. 1 is a block diagram representation of an ultrasonic probe tip component of the present invention incorporated into a micro tool having nano indentation or scanning capabilities.

Turning attention now to the Figures, embodiments of the probe tip will now be described in more detail. With Reference to FIG. 1 a schematic of a portion of a micro tool for nano scale high-frequency material characterization is shown. The micro tool includes an ultrasonic multimode probe tip component 10 coupled to a micro tool probe 202 of the invention. A sample 12 is shown positioned on an actuatable stage, scanner, or table 210 of known suitable construction. Movement of the stage 210 is controlled by controller 208. Sensing unit 204 is coupled to the probe 202 and central control unit or processor 206. Sensing unit 204 receives input and provides feedback controls to components of the micro tool probe 202. The ultrasonic probe tip 10 is electrically coupled to amplifier 14, signal processor 16 and central control unit 206. The micro tool probe, sensing unit, control unit 206, probe tip 10, amplifier 14, signal processor 16, stage 210, and stage controller 208 are coupled via electrical conduits 62-76.

In an embodiment of the invention the nano scale high-frequency characterization micro tool device operates as a nano indentation device. A user may use central controller 206 to position the sample 12 and ultrasonic probe tip 10 so that an end portion of the probe tip 10 pushes (at a micro dimension) into the surface of the sample 12. The controller 206 may then provide a command to control oscillation of the probe tip 10 at a resonance mode driven by the signal processor 16 and amplifier 14. The resulting wave signals of the oscillating tip 10 are received and processed. This analog high frequency output signal is a function of a true contact cross-section area, hardness, elastic constants, friction coefficient and adhesion of the sample 12.

Figure 2:
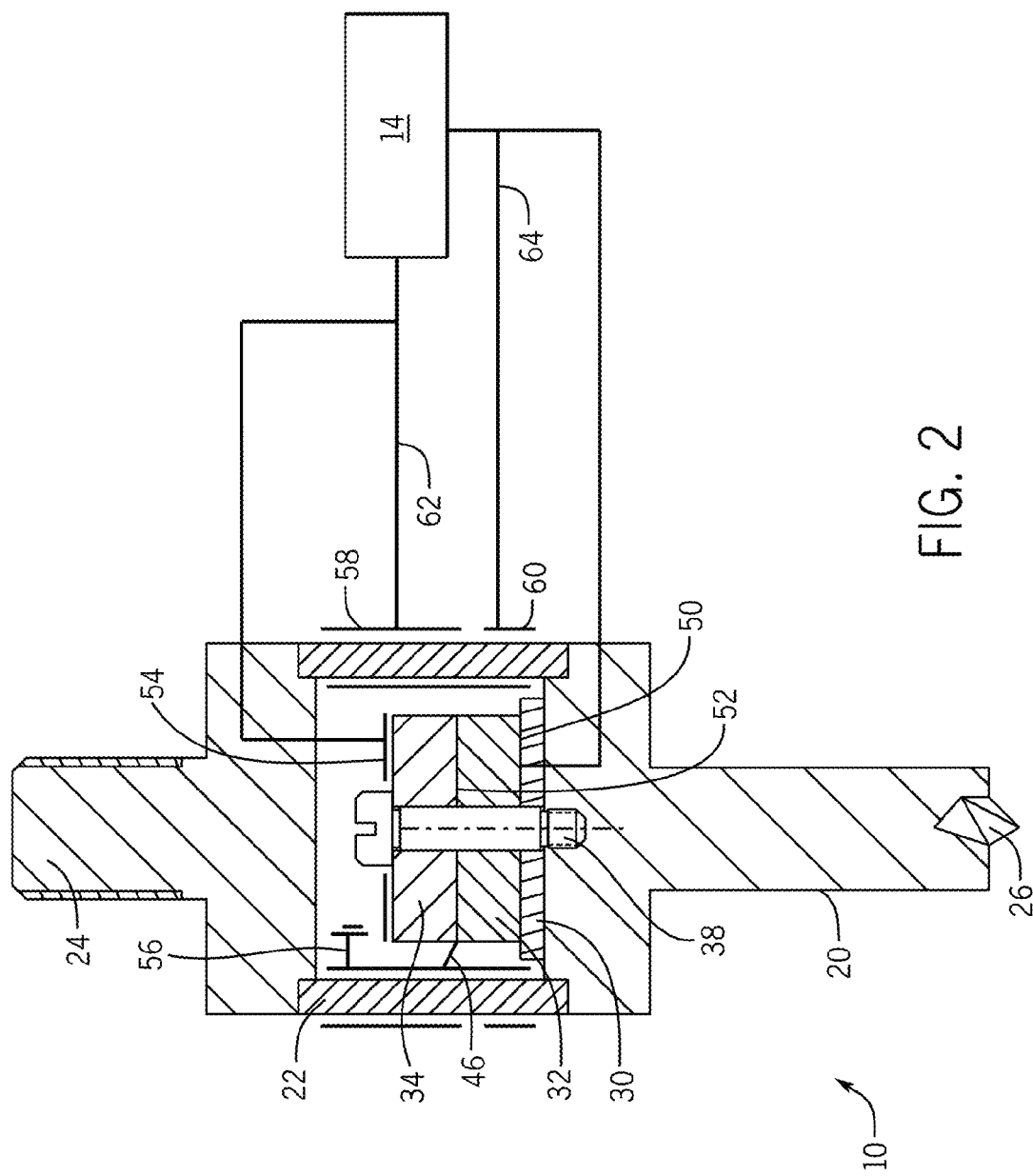
FIG. 2 is a partial sectional front view of a probe tip in accordance with an embodiment of the invention.

Referring to FIG. 2, an embodiment of the ultrasonic probe tip component 10 is shown in greater sectional detail. The probe tip 10 includes an elongated column or waveguide 20 fixed to a sheath 22 that is fixed to coupling member 24. A diamond tip insert 26 extends from an end of the waveguide 20. The ultrasonic wave generator comprises a first piezo ceramic disc positioned on the waveguide 20 and the ultrasonic wave receiver is comprised of a second piezo ceramic disc positioned on the waveguide 20. An insulating layer or isolator 30 is positioned between the waveguide 20 and the wave generator and receiver. An electrode 50 is sandwiched between isolator 30 and piezo ceramic disc 32. Electrode 50 transmits the energy required to stimulate piezo 32 which may generate ultrasonic waves that may be fine-tuned to resonant frequencies for the device. The piezo ceramic disc 34 is stacked above the piezo 32 and is electrically isolated from piezo 32 by a grounded electrode layer 52 sandwiched between the first and second piezo ceramic discs. Electrode layer 52 is electrically connected via lead 46 to grounded electrode 56. An electrode 54 is positioned on the top side of the second piezo and is used to transmit energy to and from the piezo ceramic disc 34.

Excitation of the piezo at certain frequencies will cause the waveguide 20 to vibrate longitudinally while other frequencies will cause the waveguide to oscillate with a torsional rotation. The tip 26 may be further rotated by applying sufficient energy to spaced apart electrodes 58 and 60 positioned on piezo ceramic sheath 22 so that a torsional oscillation results at certain frequencies. The sheath 22 is grounded by electrode 56. Electrical lead 62 connects amplifier 14 to both the longitude electrode 54 and the oscillating electrode 58. Likewise, electrical lead 64 connects amplifier 14 to both longitudinal electrode 50 and oscillating electrode 60.

Figure 3:
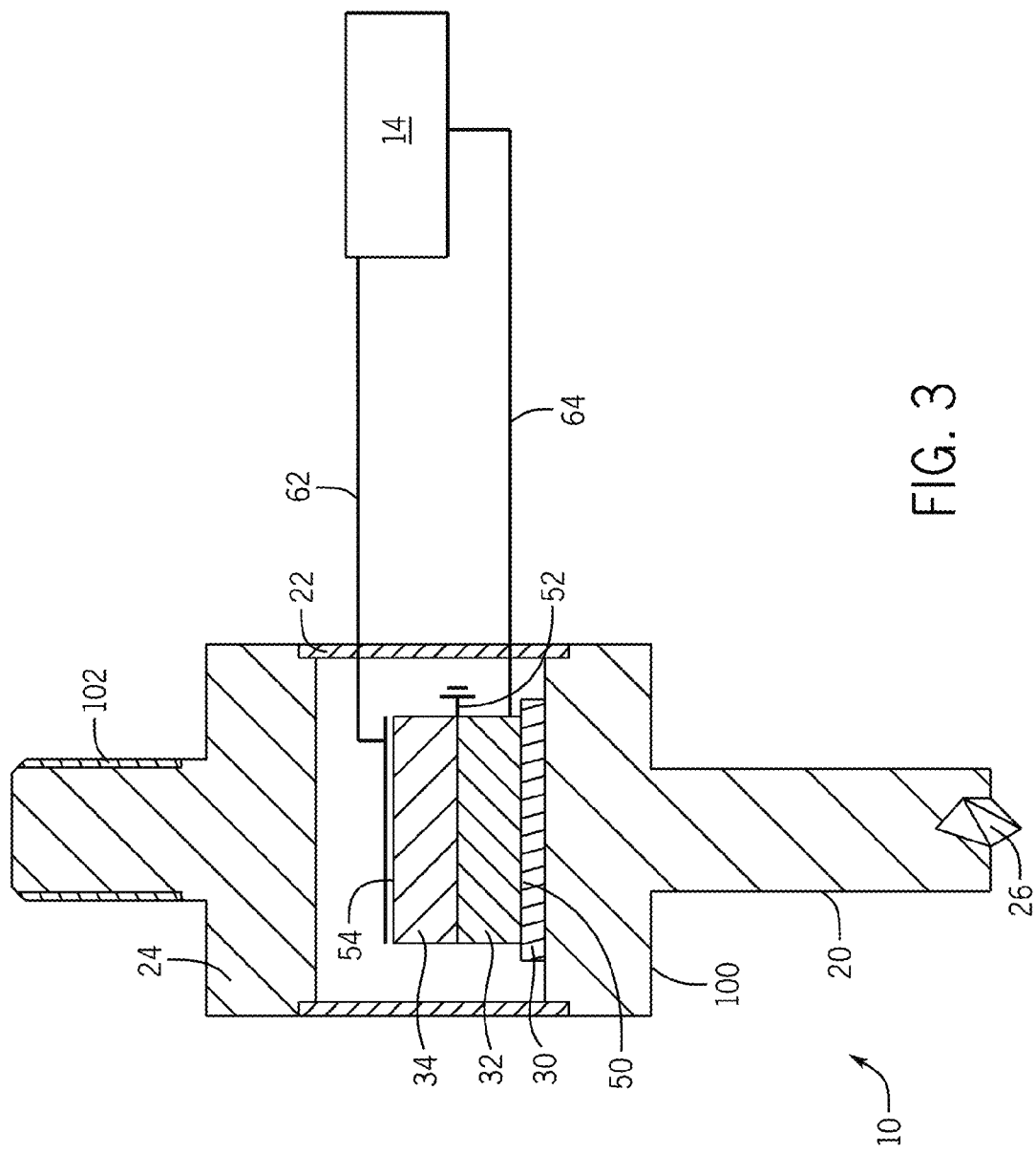
FIG. 3 is a partial sectional front view of a probe tip in accordance with an embodiment of the invention.

In an embodiment of the ultrasonic probe tip component 10 shown in FIG. 3, the probe tip 10 includes an elongated column or waveguide 20 extending from cylindrical base 100. An opposing side of the base 100 is fixed to a sheath 22 that is fixed to coupling member 24. A diamond tip insert 26 extends from an end of the waveguide 20. The ultrasonic wave generator comprises a first piezo ceramic disc positioned on the base 100 of waveguide 20 and the ultrasonic wave receiver is comprised of a second piezo ceramic disc positioned on the base 100 of the waveguide 20. An insulating layer or isolator 30 is positioned between the waveguide 20 and the wave generator and receiver. An electrode 50 is sandwiched between isolator 30 and piezo ceramic disc 32. Electrode 50 transmits the energy required to stimulate piezo 32 which may generate ultrasonic waves that may be fine-tuned to resonant frequencies for the device. The piezo ceramic disc 34 is stacked above the piezo 32 and is electrically isolated from piezo 32 by a grounded electrode layer 52 sandwiched between the first and second piezo ceramic discs. An electrode 54 is positioned on the top side of the second piezo and is used to transmit energy to and from the piezo ceramic disc 34. The electrodes 50 and 54 are electrically coupled to the signal amplifier 14 via electrical leads 64 and 62.

Figure 4:
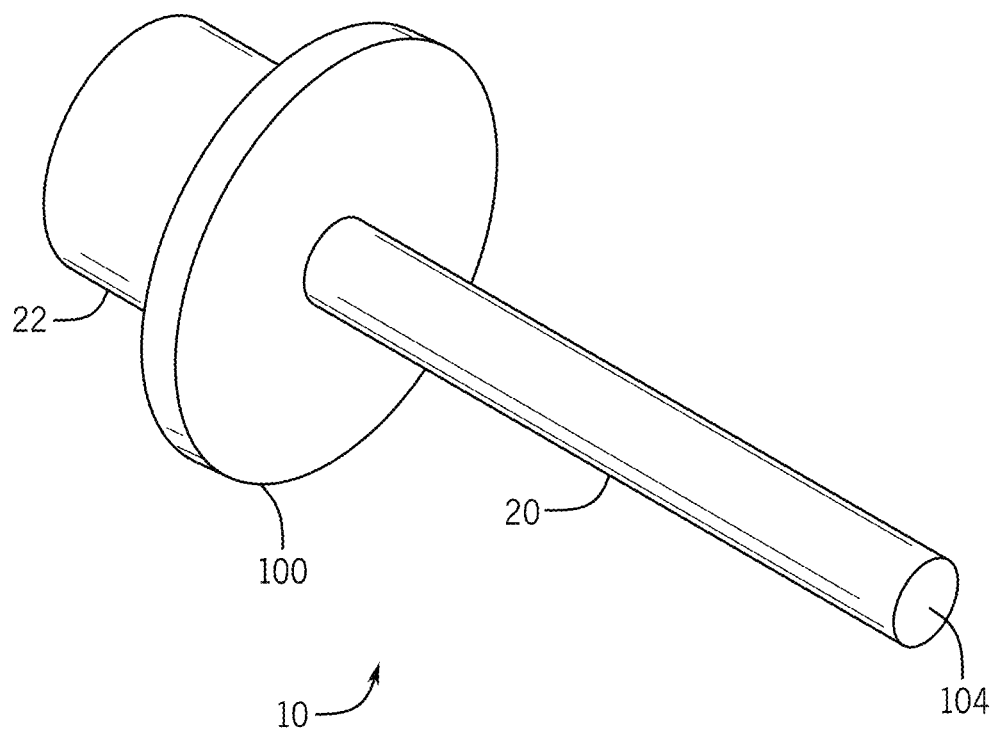
FIG. 4 is an enlarged front elevational perspective view of a probe tip in accordance with an embodiment of the invention.
Figure 5:
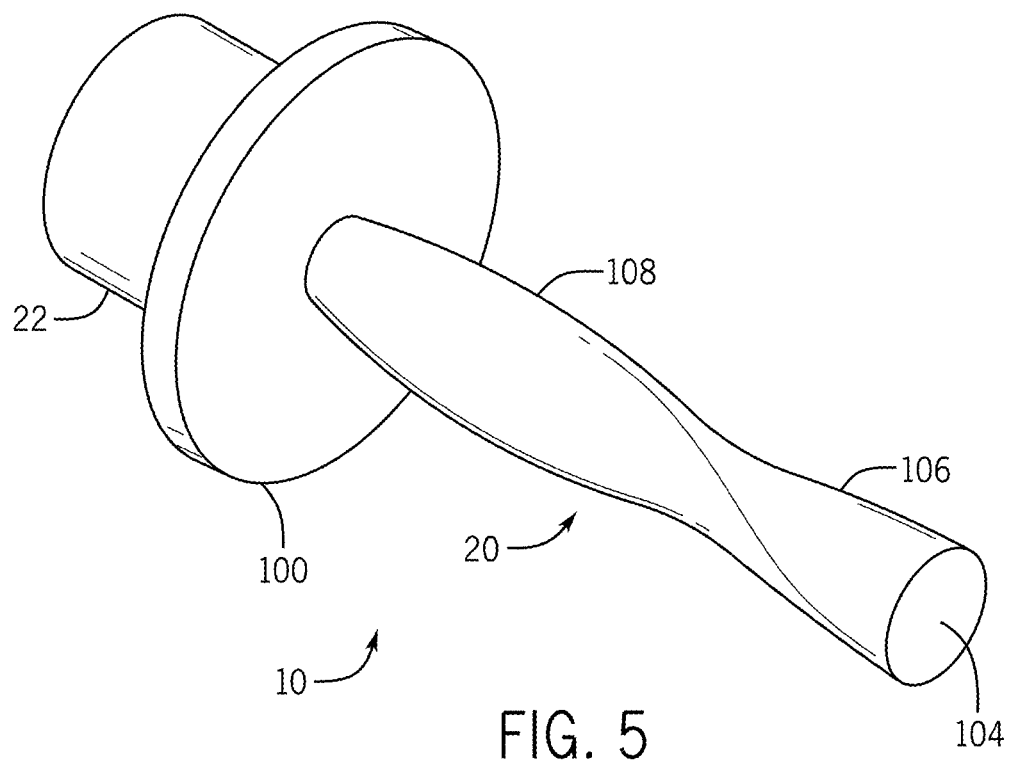
FIG. 5 is an enlarged front elevational perspective view of a probe tip in accordance with an embodiment of the invention having a harmonic frequency mode that includes a rotational propagation of the elongated column.
Figure 6:
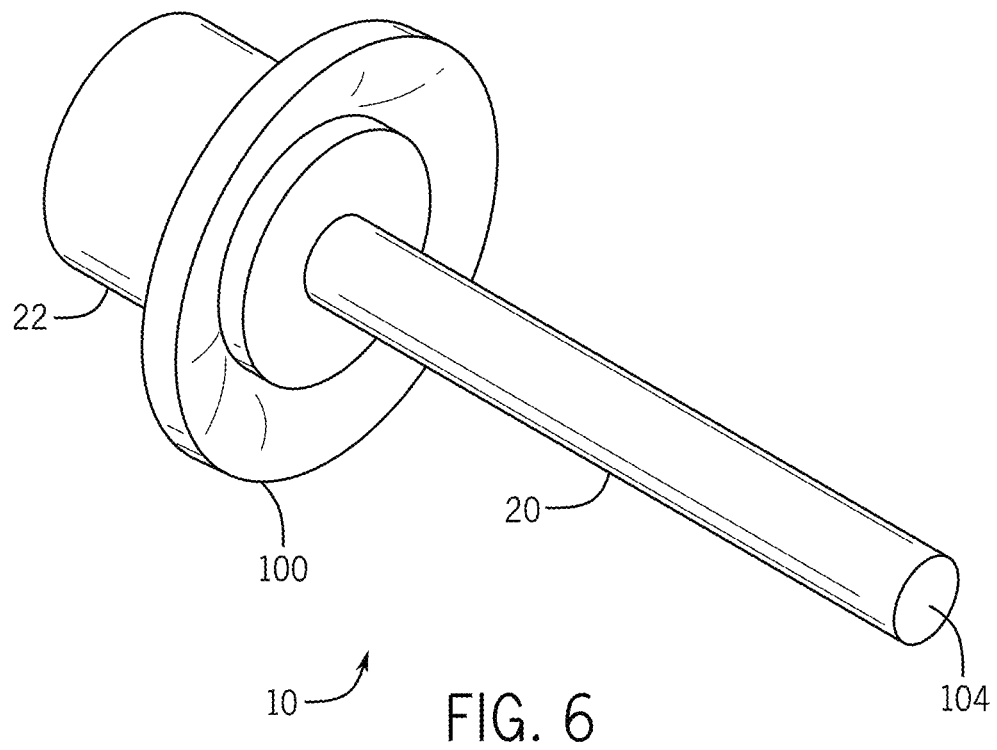
FIG. 6 is an enlarged front elevational perspective view of a probe tip in accordance with an embodiment of the invention having a harmonic frequency mode that includes a longitudinal propagation of the elongated column.

FIGS. 4-6 illustrate the longitudinal vibration and torsional oscillation as waves propagate through the waveguide 20. Utilizing a Finite Element Method (FEM), the resonance modes and modal shapes of longitudinal vibration and rotational oscillation may be determined for a waveguide having a predefined radius and length and made of a particular material. FIGS. 4 and 6 illustrate resonant frequencies of 287414 Hz and 748258 Hz that result in longitudinal vibration of the waveguide. FIG. 5 illustrates a resonant frequency at 499050 Hz that results in a rotational oscillation of the waveguide. Position 106 on the waveguide represents a node and position 108 represents an antinode as waves propagate through the waveguide at this resonant frequency. Boundary conditions of resonant frequencies for longitudinal vibration and rotational oscillation may be determined for the waveguide. When the waveguide is oscillated at or approximate to a resonance mode the sensitivity of the tool is increased.

Figure 7:
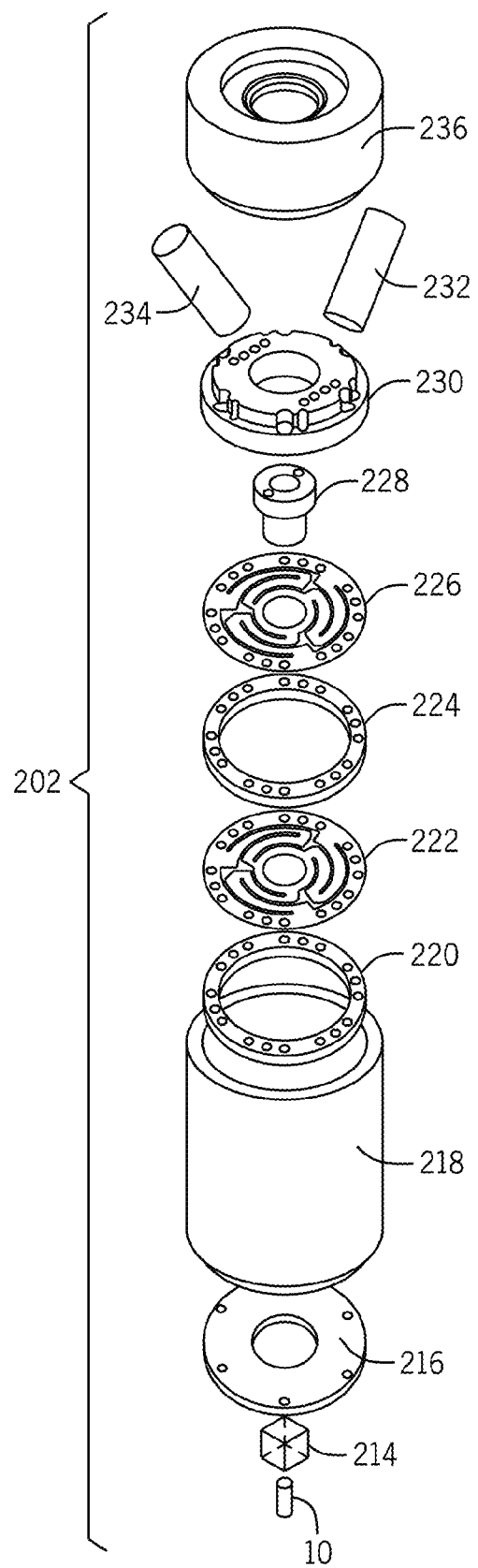
FIG. 7 is an exploded perspective view of a tip in accordance with an embodiment of the invention adapted to a probe of a micro tool in accordance with the invention.
Figure 8:
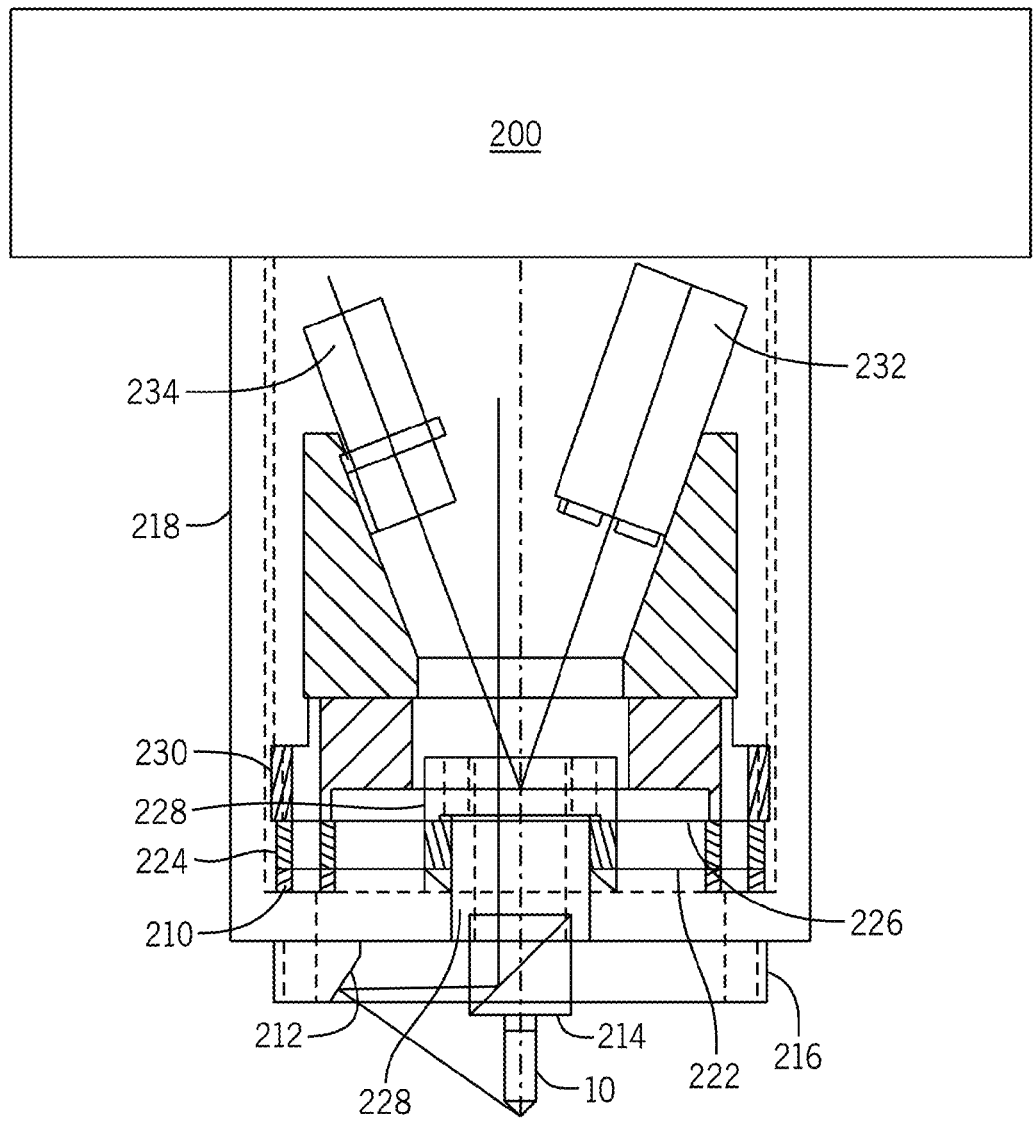
FIG. 8 is a partial sectional perspective view of a probe tip in accordance with an embodiment of the invention adapted to a head of a micro tool in accordance with the invention.
Figure 15:
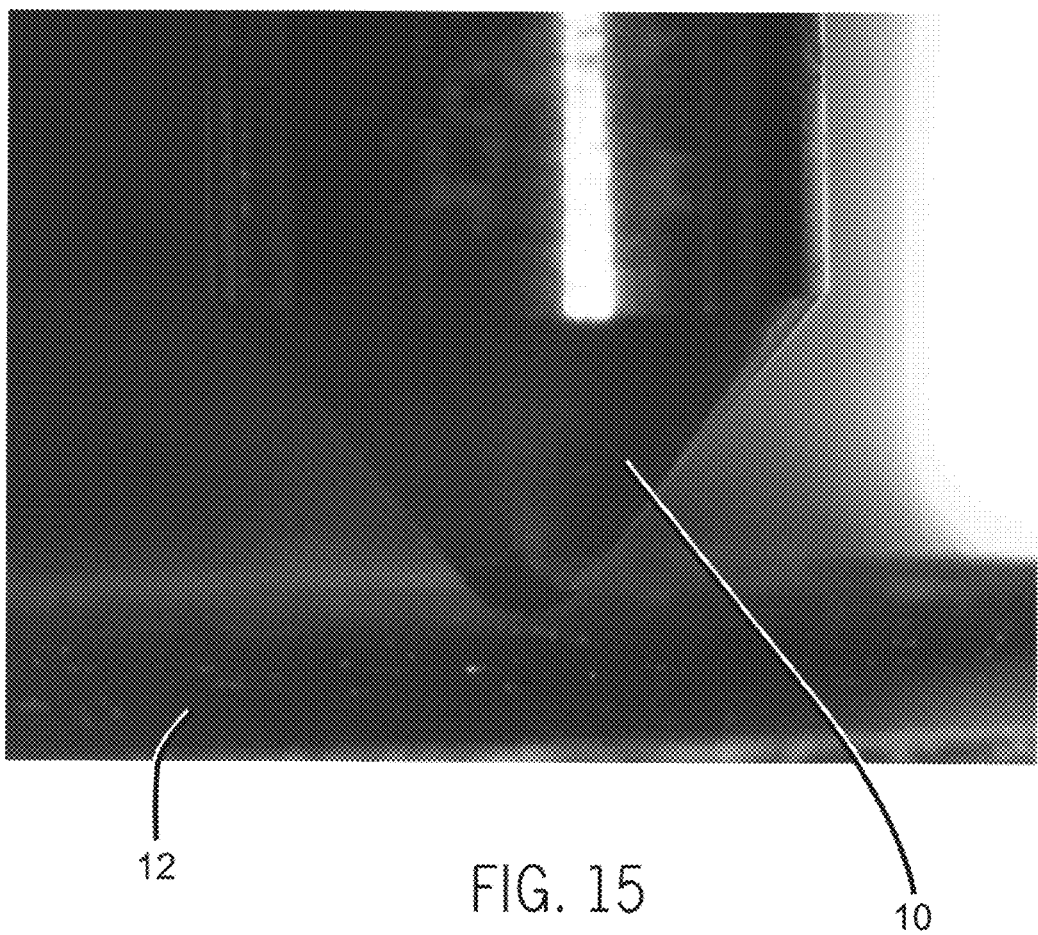
FIG. 15 is a photo illustrating a side view of the sample and a probe tip of the present invention utilizing a microtool probe of the present invention.

Referring now to FIGS. 7 and 8 a micro tool probe 202 of suitable construction of the invention is illustrated. The probe 202 includes probe tip 10 coupled to beam splitter, lens, or prism 214 that is positioned within an aperture of holder 228. The holder 228 is at least partially contained within casing 218. A bottom cover 216 contains the prism holder within the casing 218. A support ring 220, first planar spring 222, spacer 224, and second planar spring 226 are sandwiched within the casing 218 between an inner flange of the casing and top cover 230. The planar springs 222 and 226 may be constructed of, for example, a shape memory alloy such as a NiTi alloy and the springs are engaged to the holder 228. Alternatively, for example, the springs may be made from other alloys having a thin film piezo layer deposited on a planar surface of the spring. When electricity is applied to the shape memory alloy or piezo film, portions of the spring will bend to a preset position. In this manner the springs may be utilized to move the prism to a desired position within probe. A Laser 232 and photo detector 234 are also positioned in the casing 218 of the probe. Deflection of the laser beam may be utilized to ultimately determine a change of position of the tip 10. Housing 236 is coupled to the probe and includes a lens and camera within the micro tool head 200. Mirror 212 is held in position with bottom cover holding ring 216. Lens housing 236 may be adjusted so that light beams 240 may travel from a point off the diamond tip insert 26 and deflect off a mirror 212 to the prism 214 which directs the light beam through the probe to the camera. In this manner, a side view of the tip may be observed during nano indentation or scanning. FIG. 15 is a photo illustrating this side view of tip 10. Alternatively, the lens housing 236 may be adjusted to focus the light beams travelling from the sample so that the tip 10 in affect "disappears" from view and only the sample 12 is visible.

The microtool illustrated in FIGS. 7 and 8 includes laser diode 232 designed to emit focused collimated light onto the shaft 228 at a preferred angle. The laser beam reflection off the sample is detected by a photo detector quad 234 which converts it into quad voltages and calibrated displacement signal. The shaft 228 is rigidly attached on the actuating suspension springs 226, 212. Actuating springs are made of shape memory alloy or spring sheet material with piezo-active patches on the spring segments. Spacer 224 and top 230 and bottom 220 covers have threaded holes for screws (not shown) which keep all the assembly in place. The assembly is rigidly inserted into an objective barrel 218 and closed with bottom cover 216. Transparent prism or lens 214 is rigidly attached to the bottom of the shaft 228. The ultrasonic or regular nano-indentation tip 10 is installed or coupled to the prism/lens 214.

Those skilled in the art will appreciate that the microtool nano-indentation/scratch instrument 202 shown in FIGS. 7 and 8 can be operated as a stand-alone instrument installed on precision positioning stages. Alternatively, nanoindentation/scratch instrument 202 can be installed as an objective on an optical microscope to expand the capabilities and versatility of the microscope and to measure mechanical materials properties down to nanometer scale. Further, a "see-through" nanoindenter facilitates real-time precision positioning of the sample. This see-through feature is beneficial when characterizing multiphase materials or MEMS devices. The tool may be adjusted to also view a side of the tip which could be useful when measuring adhesion and contact angle.

The actuating springs 222 and 226 integrated into a nanoindentation instrument enables precision and active positioning. The spring's actuation may be accomplished using shape memory alloy or piezo patches allowing for a compact actuator with significantly less thermal drift. To actuate the springs an electrical voltage potential is applied on the outer and inner diameter of the springs or top and bottom electrode of the piezo patch. Due to materials properties of shape memory alloy or piezo springs the springs shape changes, either expanding or contracting, thereby producing vertical displacement of the shaft 228 and displacing laser beam. The voltage potential may be increased or decreased to displace the laser at known desired increments and tracked by a photo detector 234. By way of example, the voltage potential and photo diode output may be calibrated and converted into loading-unloading curves whereby material properties may be derived using classical contact mechanics principles.

Figure 9:
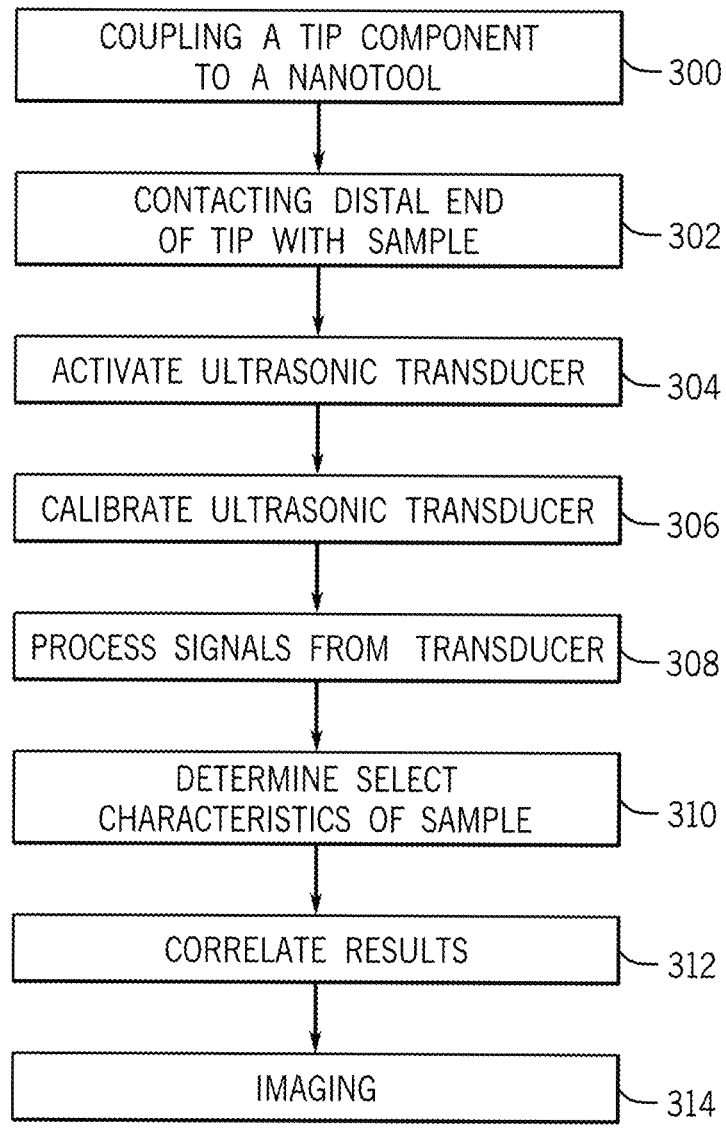
FIG. 9 is a flowchart illustrating a method in accordance with the present invention.
Figure 10:
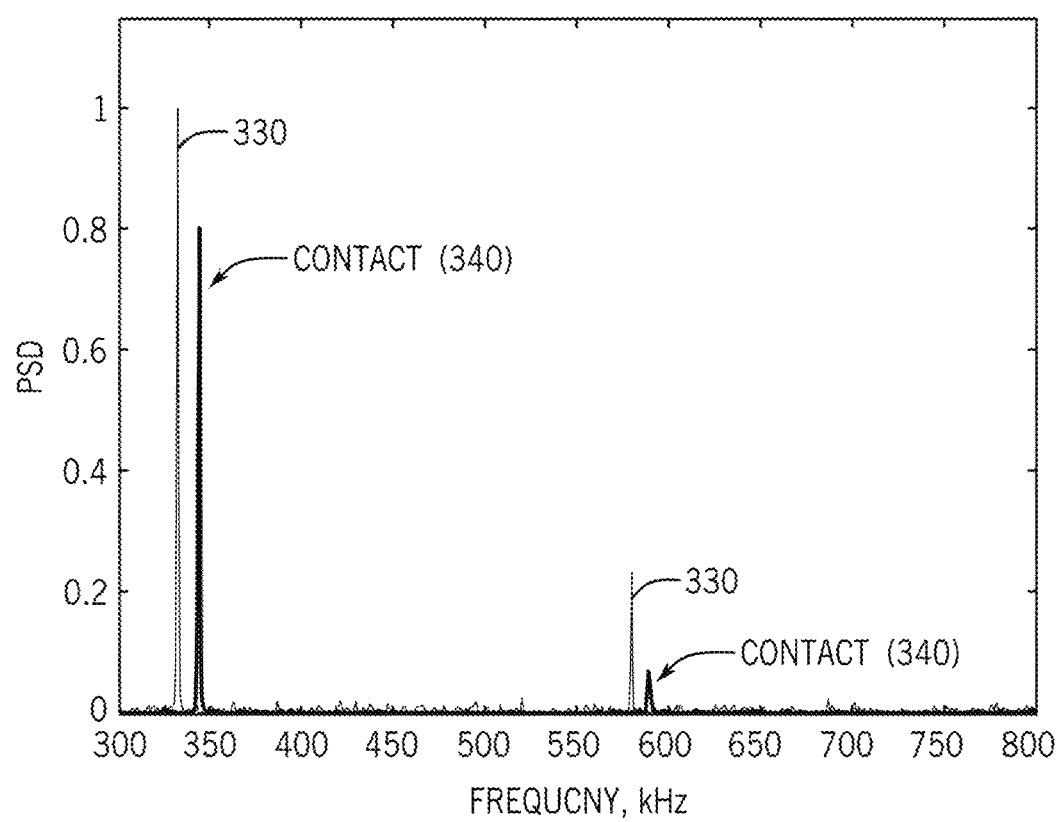
FIG. 10 is a graph illustrating a comparison of waves detected by a tip of the present invention during contact and without contact.
Figure 11:
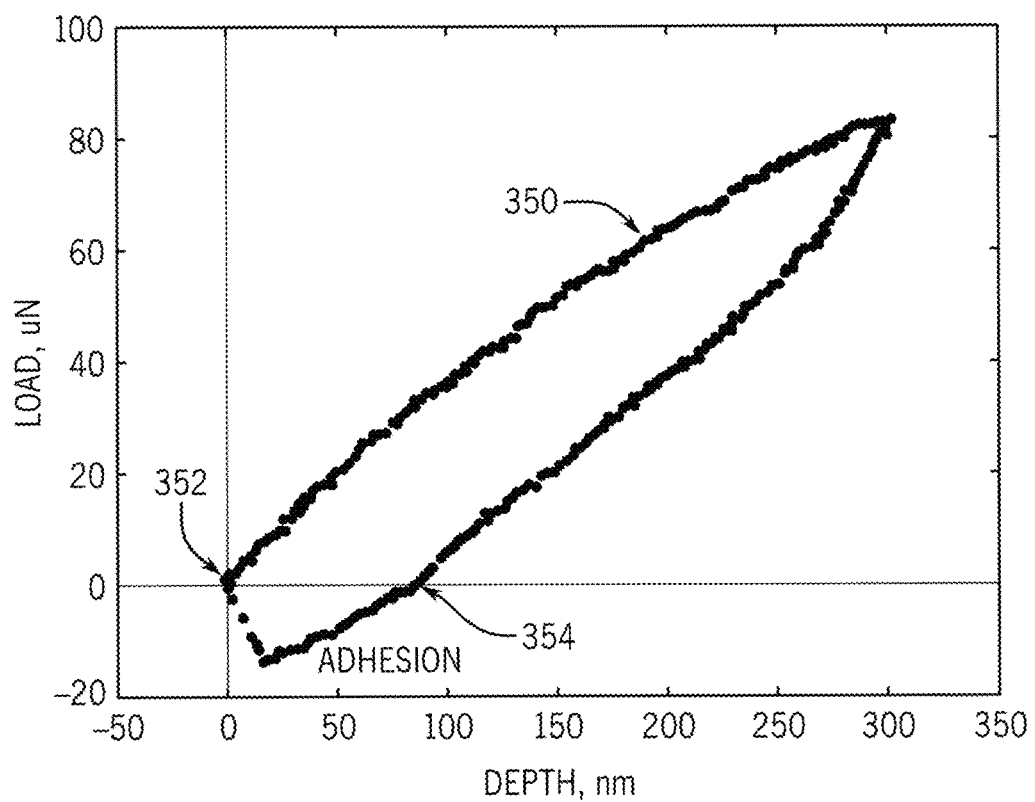
FIG. 11 is a graph illustrating a displacement of the tip of the present invention in comparison to the force applied to the tip.
Figure 12:
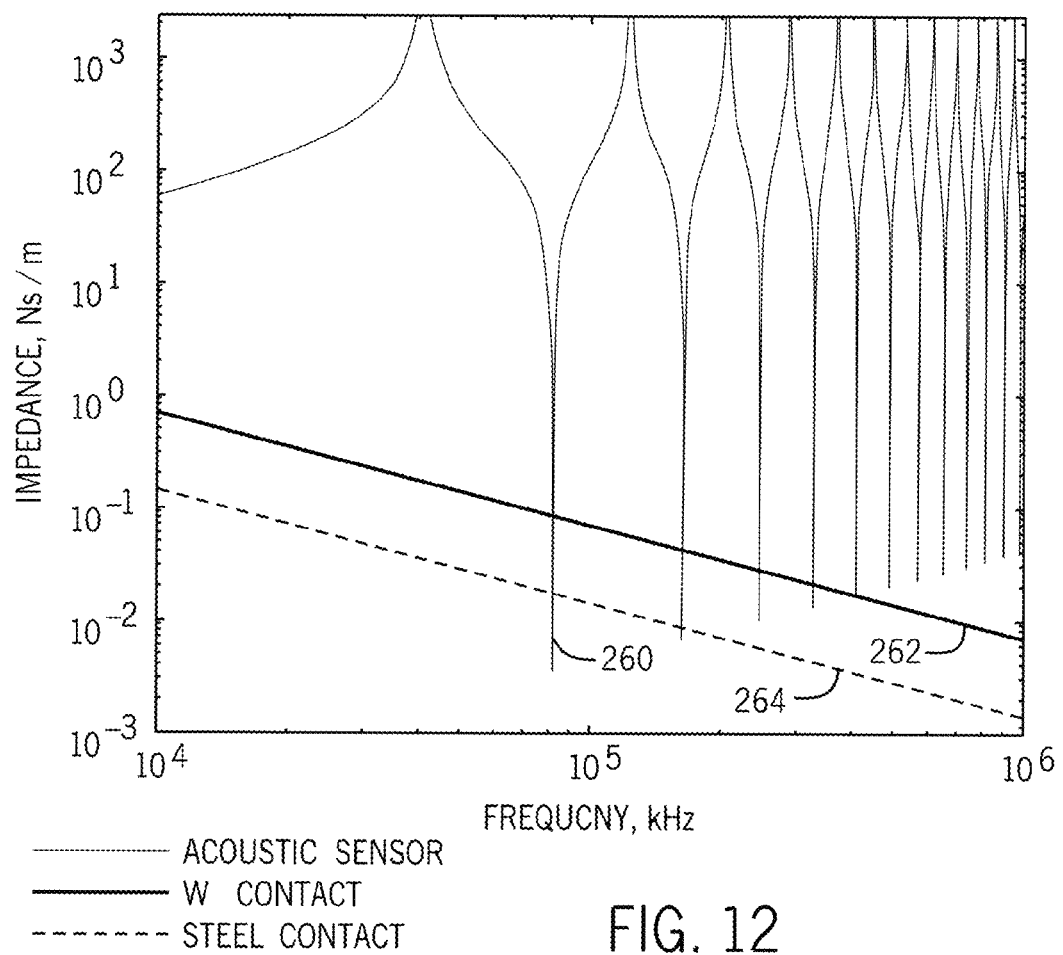
FIG. 12 is a graph illustrating theoretical curves of mechanical impedance and contact impedance.
Figure 13:
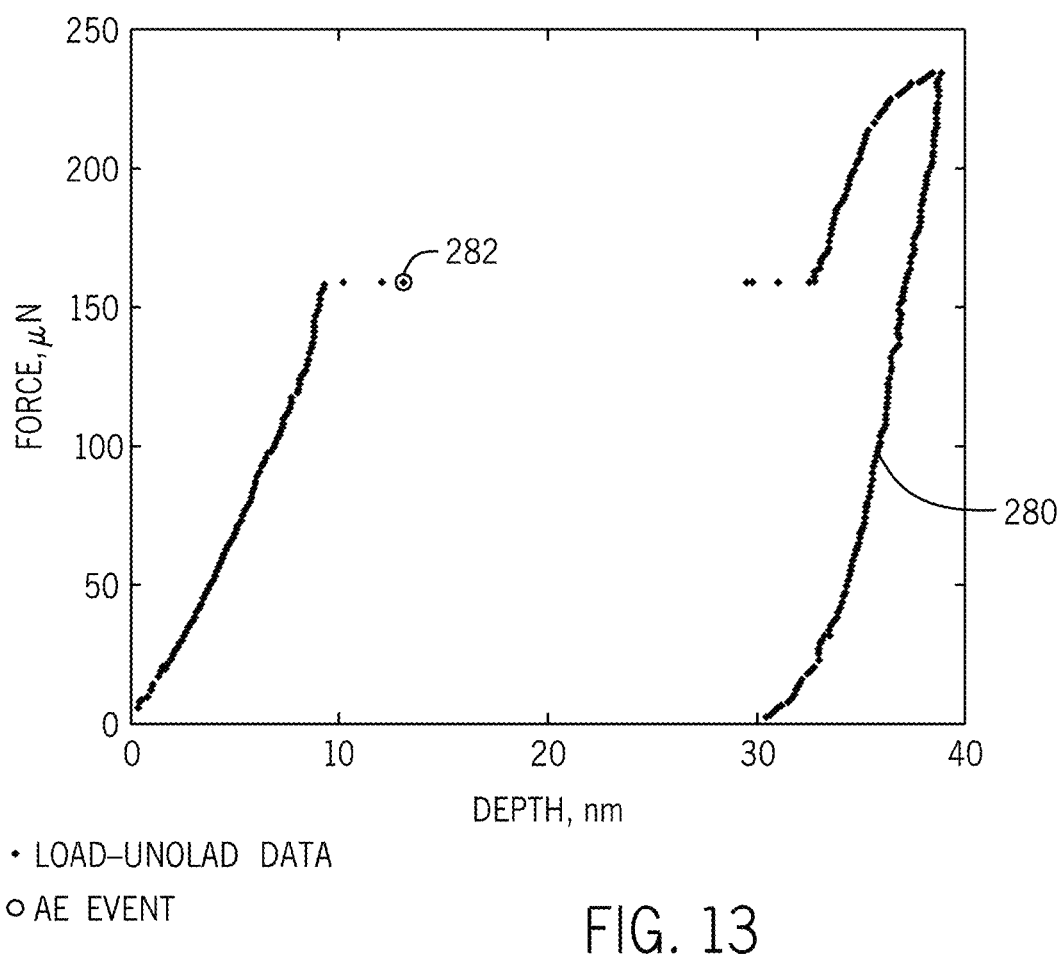
FIG. 13 is a graph illustrating passive acoustic monitoring results using the probe tip of the present invention.
Figure 14:
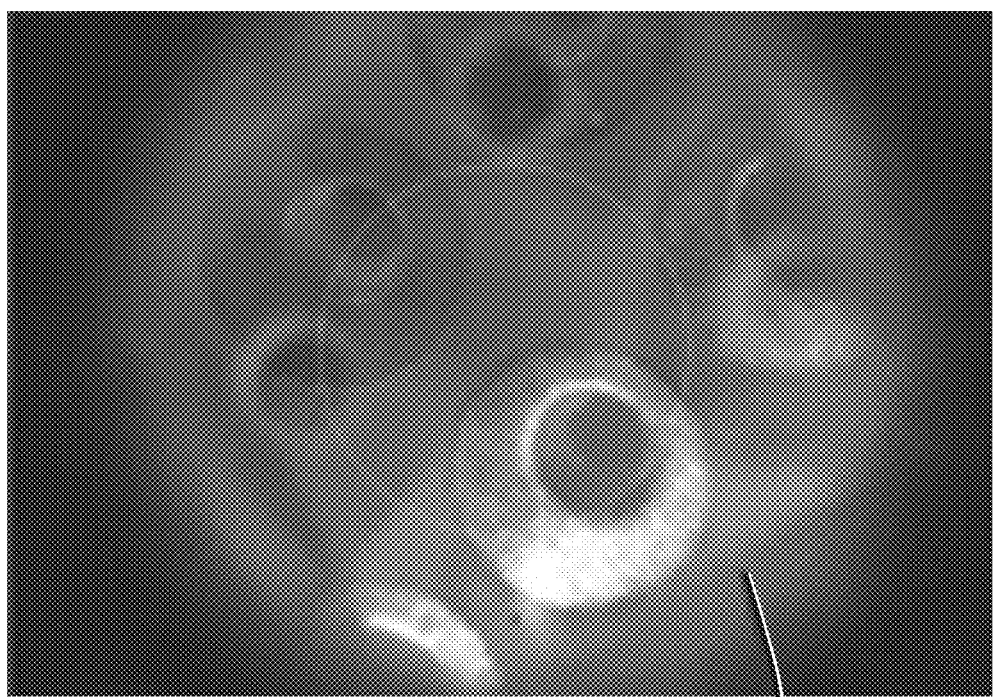
FIG. 14 is a photo illustrating a top down view of a sample utilizing a microtool probe of the present invention.

In use, the method illustrated in FIG. 9 may be implemented. First, the user selects a probe tip of the invention that includes an elongated column having a free distal end, a base from which the elongated column extends, an ultrasonic transducer coupled to the base on a side opposing the elongated column, and a coupling member for coupling the base of the tip to the tool. The user then couples the probe tip to a selected nano scale tool as at 300. Once coupled the tool and tip are actuated to make contact with the sample to determine a mechanical impedance of the sample 302. The ultrasonic transducer is then activated at 304 and the transducer is calibrated 306 by finding the boundary conditions and resonant frequencies for longitudinal vibration and rotational oscillation of the tip. Once calibrated, when the tip contacts the sample, changes in the detected ultrasonic waves may be signal processed 308 and utilized to determine material characteristics of the sample 310. FIG. 10 illustrates the change in amplitude and phase of an ultrasonic wave when the tip is in contact 340 and not in contact 350 with the sample. Ultrasonic tip power spectral density (PSD) is plotted against measured frequency. Frequency shift on 2 vibrational modes is observed due to the contact with a steel sample and non-contact condition. Frequency shift can be calibrated to the contact area and hardness of the surface as given below in Eq. (6). Further, FIG. 11 illustrates that the adhesion of a material may be determined by comparing the force exerted on the sample to the amount of displacement. The displacement curve 350 illustrates that the measurable displacement as force is increased from zero 352 and decreased is non-linear 354 due to adhesion properties of a material. The adhesion portion of the curve is de-picked by the negative force segment. FIG. 12 illustrates theoretical curves (calculated from equations 2, 3, and 5) expected from the ultrasonic tip 10 corresponding to mechanical impedance Zv (Acoustic Sensor) 260 and nanoscale contact impedances of Tungsten (W) 262 and steel contact curve 264. The theoretical curves 260, 262, and 264 suggests that Acoustic sensor impedance from the tip of the present invention matches W and steel contact impedance at 180 kHz, 270 kHz 320 kHz which in general agrees with measured FEM result and as illustrated above in FIGS. 4 and 6. FIG. 13 illustrates measured passive acoustic monitoring result using the ultrasonic tip 10 in listening mode only. The acoustic event is correlated with nanoindentation load-unload data on the W sample. Thus, the onset of plasticity induced passive acoustic event (AE) 282 correlates with an excursion on load-unload data 280.

Once the material characteristics of a sample are determined these results may be correlated 312 and imaging created based on the results 314. Further, the signals received by said ultrasonic transducer may be utilized to determine an approximation of a topology of the sample. When using an SPM with quasi-static feedback the ultrasonic multimode transducer signals may be processed to determine images that represent the materials properties in two-dimensions for the entire scanning field.

The calibrating step 306 may further include adjusting the ultrasonic transducer so that waves propagate through the elongated column at a resonant frequency with a range of frequencies between 100 kHz to 2 MHz. A particular resonant frequency within this range may be preferred for select characterizations of the sample. Also, the method according to the invention may be implemented by surface scanning the sample and simultaneously determining sample characteristics. Also, an electrical resistance of a sample may be determined dependent upon the signals received by said ultrasonic transducer.

The probe tip may also be coupled to a nano indenter micro tool. When coupled to a nano indenter or scratch instrument, a user may carry out additional measurements simultaneously with nano indentation tests specified by ISO, ASTM standards, or proposed nano scratch standards. For example, while nano indenting or scratching a material, the ultrasonic probe tip 10 may also be utilized to measure and compare contact impedance of the sample to the mechanical impedance of the oscillating ultrasonic tip. The harmonic resonant frequencies of the probe tip of the present invention allows determination of material characteristics of hard solids and thin coatings.

The basis for determining select material characteristics will next be presented. By definition, mechanical impedance Z is a ratio of driving force F and resultant velocity v. The mechanical impedance Z may be derived at the driving point or at the point of dynamical interaction between the oscillating probe tip 10 and sample 12. The mechanical impedance may be expressed as:

$$Z = \frac{F}{v} \quad (1)$$

The force and velocity of the probe tip are measurable such that mechanical impedance may be calculated. Also, since the ultrasonic waves at a known frequency oscillate the wave guide and tip 26 the acoustic impedance may be equated with the mechanical impedance. This equality may be expressed as mechanical impedance approximates acoustic impedance when the tip is in contact with the sample:

$$Z_c \approx Z_v \quad (2)$$

$Z_c$ represents mechanical impedance and $Z_v$ represents acoustic impedance of the sample.

For frictionless dynamic contact, the contact mechanical impedance $Z_c$ of a semi-infinitive sample excited normally by means of rigid spherical indenter tip may be further equated with a dissipative term $r_c$, a complex constant j, an inertial term $m_c$, an excitation cyclic frequency $\omega$, and a contact compliance term $q_c$, where $Z_c$ can be expressed as:

$$Z_c = r_c + jm_c - j\frac{1}{\omega q_c} \quad (3)$$

The contact compliance term $q_c$ may be expressed as in terms of an elastic Hertzian contact compliance of the radius $R_c$ and corresponding cross section area $A_c$:

$$q_c = \frac{1}{2R_c}\left(\frac{1-v_c^2}{E_c} + \frac{1-v_t^2}{E_t}\right) = \frac{\sqrt{\pi}}{2\sqrt{A_c}}\left(\frac{1-v_c^2}{E_c} + \frac{1-v_t^2}{E_t}\right) \quad (4)$$

where $v_c$ represents velocity at contact, $E_c$ represents an elastic modulus at contact, $v_t$ represents a velocity at the tip, and $E_t$ represents an elastic modulus at the tip. It has been shown that for ultrasonic testing range (50-500 kHz) the terms for dissipative $r_c$ and inertia $m_c$ term in the expression for mechanical contact impedance $Z_c$ are negligibly small compared with the compliance term $q_c$. Hence, the mechanical contact impedance is approximately inversely proportional to the contact compliance $q_c$ multiplied by the excitation cyclic frequency ω.

It is further known that acoustic contact impedance $Z_c$ may be equated with the distributed parameter oscillator model in the form:

$$Z_v = vAq \tan(2\omega f_0) \tag{5}$$

where, v, A, q, ω, $f_0$ are velocity of sound, cross-section area, density of the oscillator, cyclic frequency, and resonant frequency at free state respectively. By substituting Eq. 3, 5 into Eq. 2, excluding negligible terms, and including a forced resonance state expression, the resulting contacting area $A_c$ can be evaluated as follows:

$$A_c^{0.5} = \left( \frac{1-v_s^2}{E_s} + \frac{1-v_t^2}{E_t} \right) bvAq2\pi f_c \tan(2\pi f_c / f_o) \tag{6}$$

where b is an instrument constant obtained from calibration and $f_c$ is the resonant frequency at contact. From equation 6 the nano indent hardness and E modulus of a sample may be calculated. Acoustic contact impedance matching with acoustic impedance of the sample may be accomplished for specific materials at specific loads to match mechanical impedance. Measurements can be correlated with surface hardness and carried out at 100 kHz-2 MHz range. Further, sub-surface sensing via nano indentation or surface scanning provides quantitative information on material properties such as elasticity modulus and hardness. Surface hardness imaging can also be accomplished in a slight contact e.g. SPM/AFM feedback loop.

Alternatively, when the probe tip is operated at a GHz range, the ultrasonic transducer is capable of generating and receiving Rayleigh/Lamb waves. Therefore, deriving group velocities and extracting local elastic constants such as Young's modulus is possible at these frequencies when utilizing advanced signal processing routines. Also, the probe tip may be utilized as passive acoustic monitoring through resonant frequencies ranging from 200 kHz to 10 MHz. Passive monitoring is accomplished by turning off active wave generation and amplifying the receiver signal by ~80 dB. When combined with a nano indentation/scratch micro tool the controller may be implemented to distinguish different material behaviors at nano scale such as phase transformation, onset of plasticity, twining and thin film fracture modes. Further, Rayleigh/Lamb waves may be excited with an external laser and the tip 10 may be utilized to monitor and register wave propagation. Also, Rayleigh waves may be monitored at 500 MHz frequency. In addition, electrical resistance measurement can be performed by turning off the ultrasonic wave generator and monitoring ultrasonic resistance between the tip and sample.

These and various other aspects and features of the invention are described with the intent to be illustrative, and not restrictive. This invention has been described herein with detail in order to comply with the patent statutes and to provide those skilled in the art with information needed to apply the novel principles and to construct and use such specialized components as are required. It is to be understood, however, that the invention can be carried out by specifically different constructions, and that various modifications, both as to the construction and operating procedures, can be accomplished without departing from the scope of the invention. Further, in the appended claims, the transitional terms comprising and including are used in the open ended sense in that elements in addition to those enumerated may also be present. Other examples will be apparent to those of skill in the art upon reviewing this document.

What is claimed is:

1. An ultrasonic tip system for metrology and topology tools, comprising:
   a probe tip including an ultrasonic transducer that directs ultrasonic waves towards a sample;
   a comparator to compare obtained contact acoustic impedance with measured electromechanical impedance;
   an elongated wave guide coupled to the ultrasonic transducer, said wave guide vibrates longitudinally and oscillates rotationally dependent upon a frequency of the ultrasonic waves; and
   an energy source.

2. The tip system according to claim 1, further including a coupling member to couple said tip to the tool.

3. The tip system according to claim 1, further including a controller coupled to said transducer.

4. The tip system according to claim 1, further including a diamond insert coupled to a free end of said wave guide.

5. The tip system according to claim 1, wherein a free end of said wave guide includes a contoured shape.

6. The tip system according to claim 1, wherein said wave guide is approximately cylindrical in shape.

7. The tip system according to claim 1, wherein said transducer propagates ultrasonic waves at a resonant frequency with a range of frequencies between 100 kHz to 2 MHz.

8. The tip system according to claim 1, further including a signal processor coupled to said tip to determine characteristics of the sample.

9. An ultrasonic tip component for a micro tool comprising:
   an elongated column that vibrates in a longitudinal direction and oscillates in a rotation direction dependent upon a resonant frequency propogating through the elongated column, and said elongated column having a free distal end;
   a base from which said elongated column extends;
   an ultrasonic transducer coupled to said base on a side opposing said elongated column; and
   a coupling member for coupling said base of the tip to the tool.

10. The tip component according to claim 9, further including a control system coupled to said ultrasonic transducer.

11. The tip component according to claim 9, further including a diamond tip insert coupled to the free end of said elongated column.

12. The tip component according to claim 9, wherein the free distal end of said elongated column includes a contoured shape.

13. The tip component according to claim 11, wherein said elongated column is approximately cylindrical in shape.

14. The tip component according to claim 9, wherein said ultrasonic transducer is fixed to said base with a fastener.

15. The tip component according to claim 9, wherein said ultrasonic transducer is deposited on said base.

16. The tip component according to claim 15, wherein an insulating layer is deposited between said ultrasonic transducer and said base.

17. The tip component according to claim 9, wherein said ultrasonic transducer includes a wave generator and wave receiver.

18. A method of determining characteristics of a sample comprising the steps of:
- coupling a tip component to a micro tool, wherein said tip component includes an elongated column having a free distal end, a base from which said elongated column extends, an ultrasonic transducer coupled to said base on a side opposing said elongated column, and a coupling member for coupling said base of the tip to the tool;
- contacting the free distal end of said tip component with a sample;
- activating the ultrasonic transducer;
- calibrating said ultrasonic transducer;
- processing waves received by said transducer; and
- determining a characteristic of the sample.

19. The method according to claim 18, wherein said calibrating further includes adjusting the ultrasonic transducer so that waves propagate through the elongated column at a resonant frequency with a range of frequencies between 100 kHz to 2 MHz.

20. The method according to claim 19, wherein said calibrating further includes determining boundary conditions for the resonant frequency.

21. The method according to claim 18, further including the step of utilizing advanced signal processing to determine characteristics of the sample.

22. The method according to claim 18, further including the step of surface scanning the sample while determining sample characteristics.

23. The method according to claim 18, further including generating an approximation of a topology of the sample dependent upon the signals received by said ultrasonic transducer.

24. The method according to claim 18, further including the step of determining electrical resistance of a sample dependent upon the signals received by said ultrasonic transducer.

\* \* \* \* \*